United States Patent [19]

Förster et al.

[11] Patent Number: 4,657,577
[45] Date of Patent: Apr. 14, 1987

[54] PYRIDYLOXY-PHENOXY-PROPIONIC ACID PHOSPHOROATES HAVING HERBICIDAL ACTIVITY

[75] Inventors: Heinz Förster, Wuppertal; Erich Klauke, Odenthal; Uwe Priesnitz, Solingen; Hans-Jochem Riebel, Wuppertal; Ludwig Eue, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 716,875

[22] Filed: Mar. 28, 1985

Related U.S. Application Data

[62] Division of Ser. No. 577,902, Feb. 7, 1984, Pat. No. 4,585,870, which is a division of Ser. No. 495,883, May 18, 1983, Pat. No. 4,518,416.

[30] Foreign Application Priority Data

Jun. 4, 1982 [DE] Fed. Rep. of Germany ....... 3221214
Jan. 4, 1983 [DE] Fed. Rep. of Germany ....... 3300141

[51] Int. Cl.⁴ .......................... A01N 43/40; C07F 9/58
[52] U.S. Cl. .......................................... 71/86; 71/94; 546/24; 546/291; 546/278; 546/279; 546/302
[58] Field of Search ....................... 546/24; 71/94, 86

[56] References Cited

FOREIGN PATENT DOCUMENTS

| 0044163 | 6/1981 | European Pat. Off. ............ 544/286 |
| 0003313 | 1/1977 | Fed. Rep. of Germany ...... 546/302 |
| 2714662 | 10/1977 | Fed. Rep. of Germany ...... 546/302 |
| 2732846 | 1/1978 | Fed. Rep. of Germany ...... 546/302 |
| 0032561 | 12/1980 | Fed. Rep. of Germany ...... 546/276 |

OTHER PUBLICATIONS

Foerster et al., Chem. Abstracts, vol. 100(21), Abst. No. 100:175,060e May 21, 1984.
Forster et al., Chem. Abstracts, vol. 100(25), Abst. No. 100:209628p Jun. 18, 1984.

Primary Examiner—Alan L. Rothman
Attorney, Agent, or Firm—Sprung Horn Kramer & Woods

[57] ABSTRACT

Novel substituted pyridyl-phenyl ethers of the formula

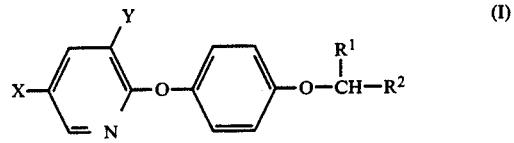

(I)

in which
X represents trifluoromethyl or chlorine,
Y represents hydrogen or chlorine,
$R^1$ represents hydrogen or methyl and
$R^2$ represents formyl or the radicals of the formulae

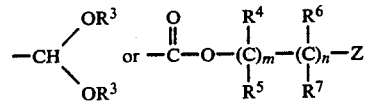

in which
$R^3$ represents alkyl with 1 to 4 carbon atoms, or the two radicals $R^3$ together represent an alkylene chain with 2 or 3 carbon atoms,
$R^4$, $R^5$, $R^6$ and $R^7$ independently of one another represent hydrogen or alkyl with 1 to 4 carbon atoms,
m represents 1 or 2,
n represents 0 or 1 and
Z represents trimethylsilyl, optionally substituted azolyl which is bonded via nitrogen or the radicals of the formulae

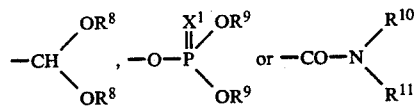

in which
$R^8$ represents alkyl with 1 to 4 carbon atoms, or the two radicals $R^8$ together represent an alkylene chain with 2 or 3 carbon atoms,
$R^9$ represents alkyl with 1 to 4 carbon atoms,
$X^1$ represents oxygen or sulphur and
$R^{10}$ and $R^{11}$ independently of one another represent hydrogen or alkyl with 1 to 4 carbon atoms, and their use as herbicides.

12 Claims, No Drawings

PYRIDYLOXY-PHENOXY-PROPIONIC ACID PHOSPHOROATES HAVING HERBICIDAL ACTIVITY

This is a division of application Ser. No. 577,902, filed Feb. 7, 1984, now U.S. Pat. No. 4,585,870, issued Apr. 29, 1986, which in turn was a division of Ser. No. 495,883, filed May 18, 1983, now U.S. Pat. No. 4,518,416, issued May 21, 1985.

The present invention relates to new, substituted pyridyl-phenyl ethers, to herbicidal compositions containing them, and to their use as herbicides.

It has already been disclosed that numerous phenoxy-propionic acid derivatives have herbicidal properties (compare DE-OS (German Published Specification) No. 2,223,894 and DE-OS (German Published Specification) No. 2,812,571).

Thus, for example, methyl 2-[4-(2,4-dichlorophenoxy)phenoxy]-propionate, ethyl 2-[4-(5-trifluoromethyl-pyridyl-2-oxy)-phenoxy]-propionate and ethyl [4-(5-trifluoromethyl-pyridyl-2-oxy)-phenoxy]-acetate can be used for combating weeds. However, the action of these substances is not always satisfactory, especially against some grasses and when low amounts are applied.

The present invention now provides, as new compounds, the substituted pyridyl-phenyl ethers of the formula

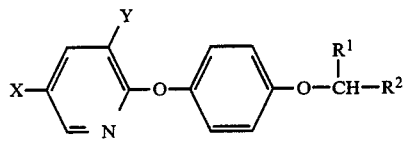

in which
X represents trifluoromethyl or chlorine,
Y represents hydrogen or chlorine,
$R^1$ represents hydrogen or methyl and
$R^2$ represents formyl or the radicals of the formulae

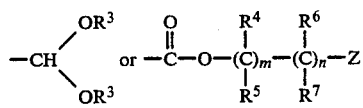

in which
$R^3$ represents alkyl with 1 to 4 carbon atoms,
or the two radicals $R^3$ together represent an alkylene chain with 2 or 3 carbon atoms,
$R^4$, $R^5$, $R^6$ and $R^7$ independently of one another represent hydrogen or alkyl with 1 to 4 carbon atoms,
m represents 1 or 2,
n represents 0 or 1 and
Z represents trimethylsilyl, optionally substituted azolyl which is bonded via nitrogen or the radicals of the formulae

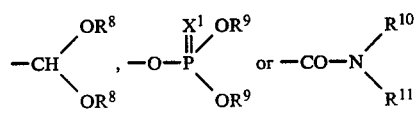

in which $R^8$ represents alkyl with 1 to 4 carbon atoms, or the two radicals $R^8$ together represent an alkylene chain with 2 or 3 carbon atoms,
$R^9$ represents alkyl with 1 to 4 carbon atoms,
$X^1$ represents oxygen or sulphur and
$R^{10}$ and $R^{11}$ independently of one another represent hydrogen or alkyl with 1 to 4 carbon atoms.

Those substituted pyridyl-phenyl ethers of the formula (I) in which $R^1$ represents methyl contain an asymmetric carbon atom in the side chain and can therefore exist in two enantiomeric forms. The invention relates both to the particular racemates and to the R- and S-enantiomers.

In this context, R-enantiomers (S-enantiomers) in each case means those optically active compounds which have the R-configuration (S-configuration) on the asymmetric carbon atom of the propionic acid unit.

The present invention also provides a process for the preparation of a substituted pyridyl-phenyl ether compound of the formula (I), in which (a) substituted pyridyl-phenyl ethers of the formula (I) are obtained by a process in which 4-(pyridyl-3-oxy)-phenols of the formula

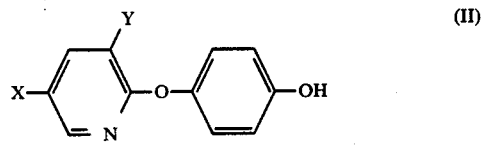

in which
X and Y have the abovementioned meaning, either
(α) are reacted with acetals of the formula

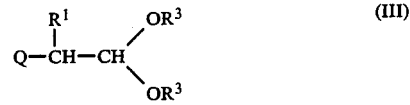

in which
$R^1$ and $R^3$ have the abovementioned meaning and
Q represents chlorine, bromine, mesylate or tosylate, if appropriate in the presence of an acid-binding agent and if appropriate in the presence of a diluent, and, if desired, the substituted pyridyl-phenyl ethers thereby formed, of the formula

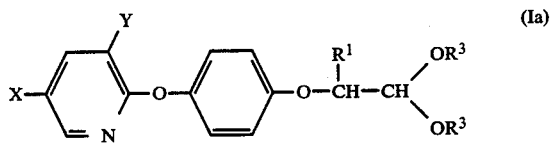

in which
X, Y, $R^1$ and $R^3$ have the abovementioned meaning, are reacted with mineral acids or carboxylic anhydrides, if appropriate in the presence of a diluent, or (β) are reacted with alkanecarboxylic acid derivatives of the formula

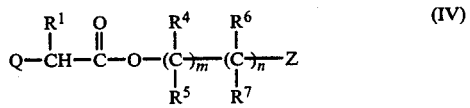

in which $R^1$, $R^4$, $R^5$, $R^6$, $R^7$, Q, Z, m and n have the abovementioned meaning,
if appropriate in the presence of an acid-binding agent and if appropriate in the presence of a diluent, (b) those substituted pyridyl-phenyl ethers of the formula (I) in which $R^2$ represents the radical of the formula

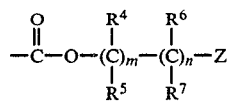

wherein

Z represents trimethylsilyl or the radical of the formula

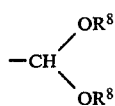

are obtained by a process in which phenoxyalkanecarboxylic acid derivatives of the formula

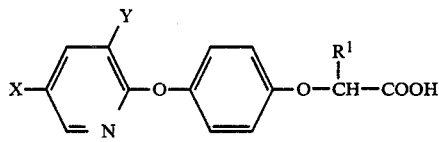

in which

X, Y and $R^1$ have the abovementioned meaning, are reacted (α) with silyl chlorides of the formula

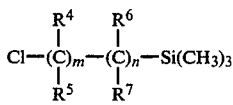

in which $R^4$, $R^5$, $R^6$, $R^7$, m and n have the above-mentioned meaning,
or (β) with acetals of the formula

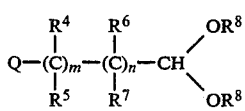

in which $R^4$, $R^5$, $R^6$, $R^7$, $R^8$, Q, m and n have the abovementioned meaning,
in each case if appropriate in the presence of an acid-binding agent and if appropriate in the presence of a diluent, and (c) those substituted pyridyl-phenyl ethers of the formula (I) in which $R^2$ represents the radical of the formula

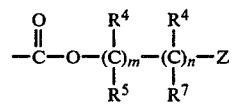

wherein

Z represents optionally substituted azolyl which is bonded via nitrogen or the radicals of the formulae

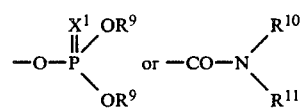

are obtained by a process wherein phenoxyalkanecarboxylic acid chlorides of the formula

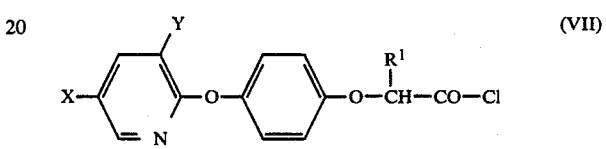

in which

X, Y and $R^1$ have the abovementioned meaning, are reacted with compounds of the formula

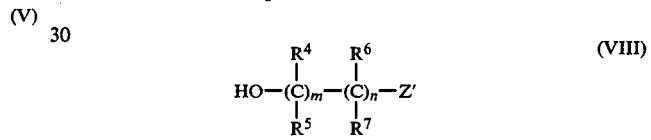

in which $R^4$, $R^5$, $R^6$, $R^7$, m and n have the above-mentioned meaning and Z' represents optionally substituted azolyl which is bonded via nitrogen or the radicals of the formulae

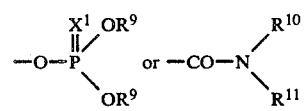

wherein $R^9$, $R^{10}$, $R^{11}$ and $X^1$ have the abovementioned meaning,
if appropriate in the presence of an acid-binding agent and if appropriate in the presence of a diluent.

Finally, it has been found that the new substituted pyridyl-phenyl ethers of the formula (I) are distinguished by an outstanding herbicidal activity.

Surprisingly, the substituted pyridyl-phenyl ethers of the formula (I) according to the invention have better herbicidal properties than methyl 2-[4-(2,4-dichlorophenoxy)-phenoxy]-propionate, which is known from the prior art and is a highly effective active compound having the same type of action. In particular, some grasses which are not dealt with by methyl 2-[4-(2,4-dichlorophenoxy)-phenoxy]-propionate can be effectively combated with the aid of the active compounds according to the invention. Furthermore, the selective herbicidal potency of the substituted pyridyl-phenyl ethers according to the invention is also superior to that of ethyl 2-[4-(5-trifluoromethyl-pyridyl-2-oxy)-phenoxy)]-propionate and that of ethyl [4-(5-trifluoromethylpyridyl-2-oxy)phenoxy]-acetate, which are structurally similar active compounds of an analogous type of action.

Formula (I) provides an unambiguous definition of the substituted pyridyl-phenyl ethers according to the invention. In this formula, X preferably represents trifluoromethyl or chlorine and Y preferably represents hydrogen or chlorine, Y especially representing hydrogen if X represents trifluoromethyl, and Y especially representing chlorine if X also represents chlorine. $R^1$ preferably represents hydrogen or methyl and $R^2$ represents formyl or the radicals of the formulae

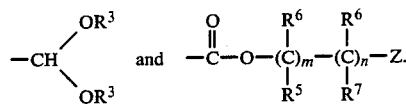

In these radicals, $R^3$ preferably represents alkyl with 1 or 2 carbon atoms, or the two substituents $R^3$ together represent an alkylene chain with 2 or 3 carbon atoms. $R^4$, $R^5$, $R^6$ and $R^7$ independently of one another preferably represent hydrogen or methyl. The index m preferably represents 1 or 2 and the index n preferably represents 0 or 1. The substituent Z preferably represents trimethylsilyl or a pyrazolyl, imidazolyl, 1,2,4-triazolyl, 1,2,3-triazolyl or 1,3,4-triazolyl radical which is bonded via a ring nitrogen atom, it being possible for each of these azolyl radicals to be mono- or poly-substituted by identical or different substituents from the group comprising fluorine, chlorine, bromine, iodine, alkyl with 1 to 4 carbon atoms, alkoxy with 1 to 4 carbon atoms and/or phenyl.

Moreover, Z preferably represents the radicals of the formulae

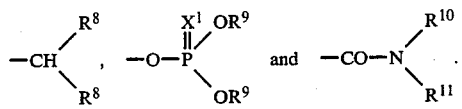

In these radicals, $R^8$ preferably represents alkyl with 1 or 2 carbon atoms or the two substituents $R^8$ together represent an alkylene chain with 2 or 3 carbon atoms. $R^9$ preferably represents alkyl with 1 to 3 carbon atoms, $X^1$ preferably represents oxygen or sulphur and $R^{10}$ and $R^{11}$ independently of one another preferably represent hydrogen or alkyl with 1 to 3 carbon atoms.

Those substances of the formula (I) in which X represents trifluoromethyl and Y represents hydrogen, or in which X and Y simultaneously represent chlorine, and $R^1$ represents hydrogen or methyl and $R^2$ represents formyl or the grouping of the formula

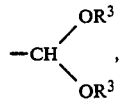

the substituents $R^3$ having those meanings which have already been mentioned above as preferred for $R^3$, are a particularly preferred group of compounds according to the invention.

Those substances of the formula (I) in which X represents trifluoromethyl and Y represents hydrogen, or in which X and Y simultaneously represent chlorine, and $R^1$ represents hydrogen or methyl and $R^2$ represents the grouping of the formula

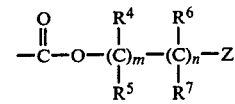

$R^4$, $R^5$, $R^6$, $R^7$, m and n having those meanings which have already been mentioned above as preferred for these radicals and indices and Z representing trimethylsilyl, are another group of particularly preferred compounds according to the invention.

Those substances of the formula (I) in which X represents trifluoromethyl and Y represents hydrogen, or in which X and Y simultaneously represent chlorine, and $R^1$ represents hydrogen or methyl and $R^2$ represents the grouping of the formula

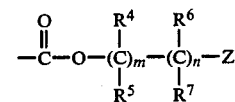

$R^4$, $R^5$, $R^6$, $R^7$, m and n having those meanings which have already been mentioned above as preferred for these radicals and indices and Z representing a pyrazolyl, imidazolyl, 1,2,4-triazolyl, 1,2,3-triazolyl or 1,3,4-triazolyl radical which is bonded via a ring nitrogen atom, it being possible for each of these azolyl radicals to be mono-, di- or tri-substituted by identical or different substituents from the group comprising fluorine, chlorine, bromine, alkyl with 1 or 2 carbon atoms, alkoxy with 1 or 2 carbon atoms and/or phenyl, are a further group of particularly preferred compounds according to the invention.

Those substances of the formula (I) in which X represents trifluoromethyl and Y represents hydrogen, or in which X and Y simultaneously represent chlorine, and $R^1$ represents hydrogen or methyl and $R^2$ represents the grouping of the formula

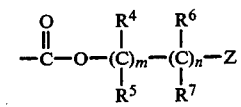

$R^4$, $R^5$, $R^6$, $R^7$, m and n having those meanings which have already been mentioned above as preferred for these radicals and indices and Z representing the grouping of the formula

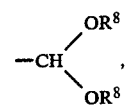

in which the substituents $R^8$ have those meanings which have already been mentioned above as preferred for $R^8$, are another group of particularly preferred compounds according to the invention.

Those substances of the formula (I) in which X represents trifluoromethyl and Y represents hydrogen, or in which X and Y simultaneously represent chlorine, and $R^1$ represents hydrogen or methyl and $R^2$ represents the grouping of the formula

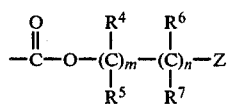

$R^4$, $R^5$, $R^6$, $R^7$, m and n having those meanings which have already been mentioned above as preferred for these radicals and indices and Z representing the grouping

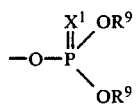

in which the substituents $R^9$ and $X^1$ have those meanings which have already been mentioned above as preferred for $R^9$ and for $X^1$, are another group of particularly preferred compounds according to the invention.

Those substances of the formula (I) in which X represents trifluoromethyl and Y represents hydrogen, or in which X and Y simultaneously represent chlorine, and $R^1$ represents hydrogen or methyl and $R^2$ represents the grouping of the formula

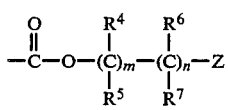

$R^4$, $R^5$, $R^6$, $R^7$, m and n having those meanings which have already been mentioned above as preferred for these radicals and indices and Z representing the grouping of the formula

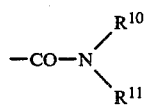

in which the substituents $R^{10}$ and $R^{11}$ have those meanings which have already been mentioned above as preferred for $R^{10}$ and $R^{11}$, are another group of particularly preferred compounds according to the invention.

The R-enantiomers of those substituted pyridyl-phenyl ethers of the formula (I) in which $R^1$ represents methyl, that is to say the compounds, according to the invention, of the formula

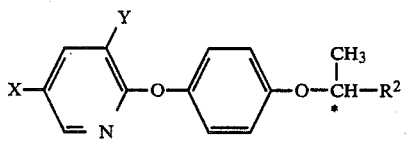

in which

X, Y and $R^2$ have the meaning given above as preferred, are also particularly preferred.

In this formula, the asymmetric carbon atom (centre of asymmetry) which has the R-configuration is characterised by a (*).

The compounds listed by way of their formulae in the tables which follow may be mentioned as examples of substituted pyridyl-phenyl ethers of the formula (I).

TABLE 1 (Ic)

| X | Y | $R^1$ |
|---|---|---|
| $CF_3$ | H | H |
| $CF_3$ | H | $CH_3$ |
| Cl | Cl | H |
| Cl | Cl | $CH_3$ |

TABLE 2 (Ia)

| X | Y | $R^1$ | $R^3$ | $R^3$ |
|---|---|---|---|---|
| $CF_3$ | H | H | $CH_3$ | $CH_3$ |
| $CF_3$ | H | $CH_3$ | $CH_3$ | $CH_3$ |
| $CF_3$ | H | H | $C_2H_5$ | $C_2H_5$ |
| $CF_3$ | H | $CH_3$ | $C_2H_5$ | $C_2H_5$ |
| $CF_3$ | H | H | —$CH_2$—$CH_2$— | |
| $CF_3$ | H | $CH_3$ | —$(CH_2)_3$— | |
| $CF_3$ | H | H | —$(CH_2)_3$— | |
| $CF_3$ | H | $CH_3$ | —$CH_2$—$CH_2$— | |
| Cl | Cl | H | $CH_3$ | $CH_3$ |
| Cl | Cl | $CH_3$ | $CH_3$ | $CH_3$ |
| Cl | Cl | H | $C_2H_5$ | $C_2H_5$ |
| Cl | Cl | $CH_3$ | $C_2H_5$ | $C_2H_5$ |
| Cl | Cl | H | —$CH_2$—$CH_2$— | |
| Cl | Cl | $CH_3$ | —$(CH_2)_3$— | |
| Cl | Cl | H | —$(CH_2)_3$— | |
| Cl | Cl | $CH_3$ | —$CH_2$—$CH_2$— | |

TABLE 3 (Id)

| X | Y | $R^1$ | $R^4$ | $R^5$ | $R^6$ | $R^7$ | m | n |
|---|---|---|---|---|---|---|---|---|
| $CF_3$ | H | H | H | H | H | H | 1 | 1 |
| $CF_3$ | H | H | H | H | — | — | 1 | 0 |
| $CF_3$ | H | $CH_3$ | H | H | H | H | 1 | 1 |
| $CF_3$ | H | $CH_3$ | H | H | — | — | 1 | 0 |
| Cl | Cl | H | H | H | H | H | 1 | 1 |
| Cl | Cl | H | H | H | — | — | 1 | 0 |
| Cl | Cl | $CH_3$ | H | H | H | H | 1 | 1 |
| Cl | Cl | $CH_3$ | H | H | — | — | 1 | 0 |

TABLE 4 (Ie)

| $R^1$ | $R^4$ | $R^5$ | $R^6$ | $R^7$ | m | n | Z |
|---|---|---|---|---|---|---|---|
| H | H | H | — | — | 1 | 0 | —N(pyrrole) |

TABLE 4-continued

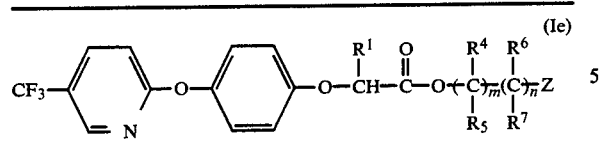

| R¹ | R⁴ | R⁵ | R⁶ | R⁷ | m | n | Z |
|---|---|---|---|---|---|---|---|
| CH₃ | H | H | — | — | 1 | 0 | pyrazol-1-yl |
| H | H | H | H | H | 1 | 1 | pyrazol-1-yl |
| CH₃ | H | H | H | H | 1 | 1 | pyrazol-1-yl |
| H | H | H | — | — | 1 | 0 | 1,2,4-triazol-1-yl |
| CH₃ | H | H | H | H | 1 | 1 | 1,2,4-triazol-1-yl |
| CH₃ | H | H | — | — | 1 | 0 | 3,5-dimethylpyrazol-1-yl |
| CH₃ | H | H | H | H | 1 | 1 | 3,5-dimethylpyrazol-1-yl |
| CH₃ | H | H | — | — | 1 | 0 | imidazol-1-yl |
| CH₃ | H | H | H | H | 1 | 1 | imidazol-1-yl |
| CH₃ | H | H | — | — | 1 | 0 | 2-methylimidazol-1-yl |

TABLE 4-continued

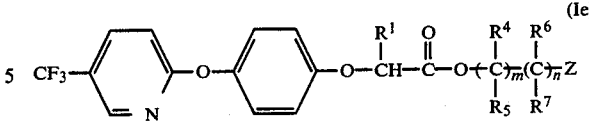

| R¹ | R⁴ | R⁵ | R⁶ | R⁷ | m | n | Z |
|---|---|---|---|---|---|---|---|
| CH₃ | H | H | H | H | 1 | 1 | 2-methylimidazol-1-yl |
| CH₃ | H | H | — | — | 1 | 0 | 3-chloro-1,2,4-triazol-1-yl |
| CH₃ | H | H | — | — | 1 | 0 | 3-methylpyrazol-1-yl |
| CH₃ | H | H | — | — | 1 | 0 | 3-chloropyrazol-1-yl |
| CH₃ | H | H | — | — | 1 | 0 | 4-chloropyrazol-1-yl |
| CH₃ | H | H | — | — | 1 | 0 | 4-methylpyrazol-1-yl |
| CH₃ | H | H | — | — | 1 | 0 | 4-methoxypyrazol-1-yl |
| CH₃ | H | H | — | — | 1 | 0 | 4-chloro-3,5-dimethylpyrazol-1-yl |
| CH₃ | H | H | CH₃ | CH₃ | 1 | 1 | 1,2,4-triazol-1-yl |
| CH₃ | H | H | CH₃ | CH₃ | 1 | 1 | pyrazol-1-yl |

TABLE 4-continued
(Ie)
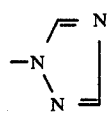
| R¹ | R⁴ | R⁵ | R⁶ | R⁷ | m | n | Z |
|---|---|---|---|---|---|---|---|
| H | H | H | CH₃ | CH₃ | 1 | 1 | 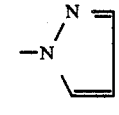 |
| H | H | H | CH₃ | CH₃ | 1 | 1 | 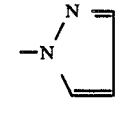 |
TABLE 5
(If)
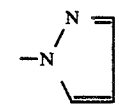
| R¹ | R⁴ | R⁵ | R⁶ | R⁷ | m | n | Z |
|---|---|---|---|---|---|---|---|
| H | H | H | — | — | 1 | 0 | 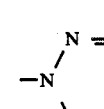 |
| CH₃ | H | H | — | — | 1 | 0 | 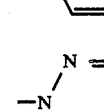 |
| H | H | H | H | H | 1 | 1 | 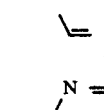 |
| CH₃ | H | H | H | H | 1 | 1 | 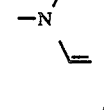 |
| H | H | H | — | — | 1 | 1 | 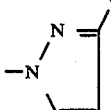 |
| CH₃ | H | H | H | H | 1 | 1 | 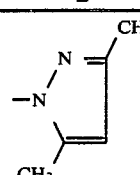 |
| CH₃ | H | H | — | — | 1 | 0 | 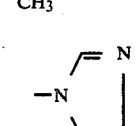 |
TABLE 5-continued
(If)
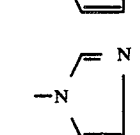
| R¹ | R⁴ | R⁵ | R⁶ | R⁷ | m | n | Z |
|---|---|---|---|---|---|---|---|
| CH₃ | H | H | H | H | 1 | 1 | 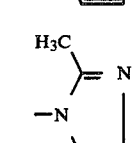 |
| CH₃ | H | H | — | — | 1 | 0 | 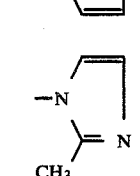 |
| CH₃ | H | H | H | H | 1 | 1 | 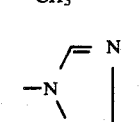 |
| CH₃ | H | H | — | — | 1 | 0 | 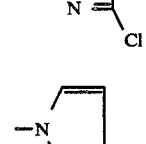 |
| CH₃ | H | H | H | H | 1 | 1 | 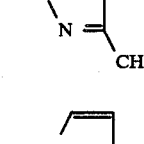 |
| CH₃ | H | H | — | — | 1 | 0 | 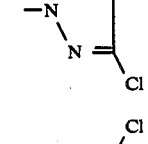 |
| CH₃ | H | H | — | — | 1 | 0 | 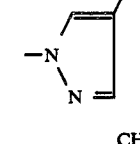 |
| CH₃ | H | H | — | — | 1 | 0 | 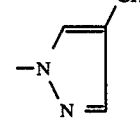 |
| CH₃ | H | H | — | — | 1 | 0 | 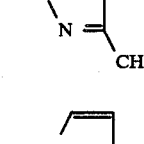 |
| CH₃ | H | H | — | — | 1 | 0 | 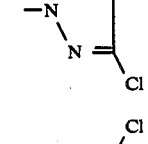 |
| CH₃ | H | H | — | — | 1 | 0 | 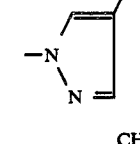 |
| CH₃ | H | H | — | — | 1 | 0 | 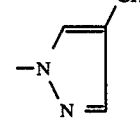 |

TABLE 5-continued (If)

| R¹ | R⁴ | R⁵ | R⁶ | R⁷ | m | n | Z |
|---|---|---|---|---|---|---|---|
| CH₃ | H | H | — | — | 1 | 0 | -N-pyrazolyl-OCH₃ |
| CH₃ | H | H | — | — | 1 | 0 | -N-pyrazolyl(CH₃,Cl,CH₃) |
| CH₃ | H | H | CH₃ | CH₃ | 1 | 1 | -N-triazolyl |
| CH₃ | H | H | CH₃ | CH₃ | 1 | 1 | -N-pyrazolyl |
| H | H | H | CH₃ | CH₃ | 1 | 1 | -N-triazolyl |
| H | H | H | CH₃ | CH₃ | 1 | 1 | -N-pyrazolyl |

TABLE 6

(Ig)

| R¹ | R⁴ | R⁵ | R⁶ | R⁷ | m | n | R⁸ | R⁸ |
|---|---|---|---|---|---|---|---|---|
| H | H | H | — | — | 1 | 0 | CH₃ | CH₃ |
| CH₃ | H | H | — | — | 1 | 0 | CH₃ | CH₃ |
| H | H | H | H | H | 1 | 1 | CH₃ | CH₃ |
| CH₃ | H | H | H | H | 1 | 1 | CH₃ | CH₃ |
| CH₃ | H | H | — | — | 1 | 0 | C₂H₅ | C₂H₅ |
| CH₃ | H | H | — | — | 1 | 0 | —CH₂—CH₂— | |
| CH₃ | H | H | — | — | 1 | 0 | —(CH₂)₃— | |

TABLE 7

(Ih)

| R¹ | R⁴ | R⁵ | R⁶ | R⁷ | m | n | R⁸ | R⁸ |
|---|---|---|---|---|---|---|---|---|
| H | H | H | — | — | 1 | 0 | CH₃ | CH₃ |

TABLE 7-continued (Ih)

| R¹ | R⁴ | R⁵ | R⁶ | R⁷ | m | n | R⁸ | R⁸ |
|---|---|---|---|---|---|---|---|---|
| CH₃ | H | H | — | — | 1 | 0 | CH₃ | CH₃ |
| H | H | H | H | H | 1 | 1 | CH₃ | CH₃ |
| CH₃ | H | H | H | H | 1 | 1 | CH₃ | CH₃ |
| CH₃ | H | H | — | — | 1 | 0 | C₂H₅ | C₂H₅ |
| CH₃ | H | H | — | — | 1 | 0 | —CH₂—CH₂— | |
| CH₃ | H | H | — | — | 1 | 0 | —(CH₂)₃— | |

TABLE 8

(Ii)

| R¹ | R⁴ | R⁵ | R⁶ | R⁷ | m | n | X¹ | R⁹ | R⁹ |
|---|---|---|---|---|---|---|---|---|---|
| H | H | H | H | H | 1 | 1 | O | CH₃ | CH₃ |
| CH₃ | H | H | H | H | 1 | 1 | O | CH₃ | CH₃ |
| H | H | H | H | H | 1 | 1 | S | CH₃ | CH₃ |
| CH₃ | H | H | H | H | 1 | 1 | S | CH₃ | CH₃ |
| CH₃ | H | H | H | H | 1 | 1 | S | C₂H₅ | C₂H₅ |
| CH₃ | H | H | H | H | 1 | 1 | O | C₂H₅ | C₂H₅ |
| CH₃ | H | H | H | H | 1 | 1 | S | C₃H₇—n | C₃H₇—n |
| CH₃ | H | H | H | H | 1 | 1 | O | C₃H₇—n | C₃H₇—n |

TABLE 9

(Ik)

| R¹ | R⁴ | R⁵ | R⁶ | R⁷ | m | n | X¹ | R⁹ | R⁹ |
|---|---|---|---|---|---|---|---|---|---|
| H | H | H | H | H | 1 | 1 | O | CH₃ | CH₃ |
| CH₃ | H | H | H | H | 1 | 1 | O | CH₃ | CH₃ |
| H | H | H | H | H | 1 | 1 | S | CH₃ | CH₃ |
| CH₃ | H | H | H | H | 1 | 1 | S | CH₃ | CH₃ |
| CH₃ | H | H | H | H | 1 | 1 | S | C₂H₅ | C₂H₅ |
| CH₃ | H | H | H | H | 1 | 1 | O | C₂H₅ | C₂H₅ |
| CH₃ | H | H | H | H | 1 | 1 | S | C₃H₇—n | C₃H₇—n |
| CH₃ | H | H | H | H | 1 | 1 | O | C₃H₇—n | C₃H₇—n |

TABLE 10

(Il)

| X | Y | R¹ | R⁴ | R⁵ | R⁶ | R⁷ | m | n | R¹⁰ | R¹¹ |
|---|---|---|---|---|---|---|---|---|---|---|
| CF₃ | H | CH₃ | H | H | — | — | 1 | 0 | CH₃ | CH₃ |
| Cl | Cl | CH₃ | H | H | — | — | 1 | 0 | CH₃ | CH₃ |
| CF₃ | H | CH₃ | H | H | H | H | 1 | 1 | C₂H₅ | C₂H₅ |
| Cl | Cl | CH₃ | H | H | H | H | 1 | 1 | C₂H₅ | C₂H₅ |
| CF₃ | H | CH₃ | H | H | — | — | 1 | 0 | C₃H₇—n | C₃H₇—n |
| Cl | Cl | CH₃ | H | H | — | — | 1 | 0 | C₃H₇—n | C₃H₇—n |

If 4-(5-trifluoromethyl-pyridyl-2-oxy)-phenol and 2-bromoacetaldehyde dimethylacetal are used as starting substances, the course of process (a, variant α) according to the invention can be represented by the following equation:

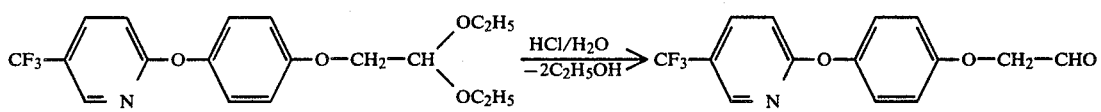

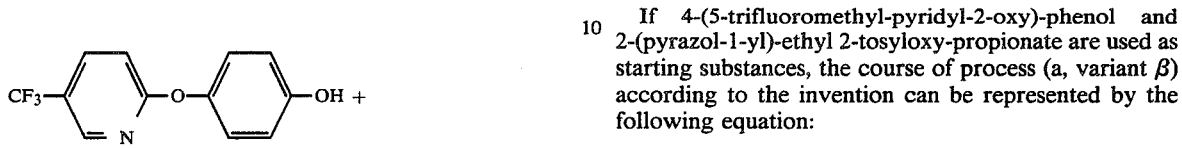

process (a, variant α) according to the invention can be represented by the following equation:

If 4-(5-trifluoromethyl-pyridyl-2-oxy)-phenol and 2-(pyrazol-1-yl)-ethyl 2-tosyloxy-propionate are used as starting substances, the course of process (a, variant β) according to the invention can be represented by the following equation:

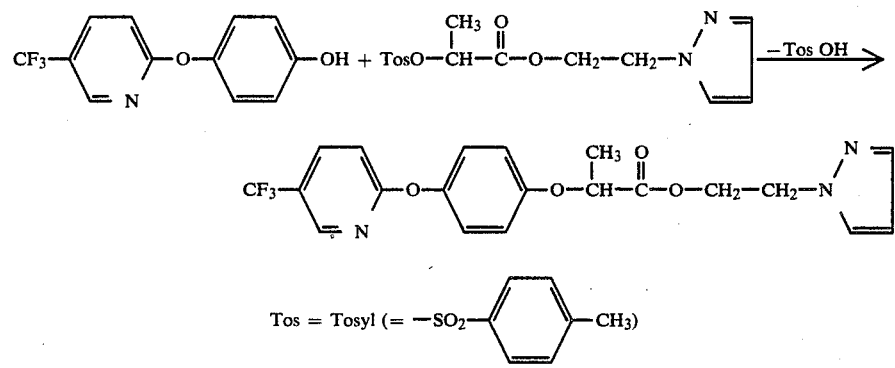

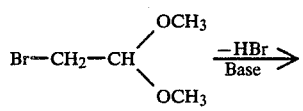

If 2-[4-(5-trifluoromethyl-pyridyl-2-oxy)-phenoxy]-propionic acid and chloromethyltrimethylsilane are used as starting substances, the course of process (b, variant α) according to the invention can be represented by the following equation:

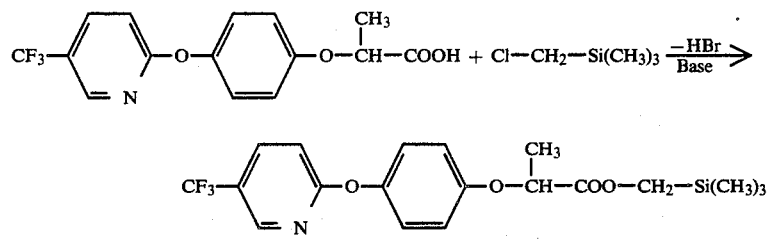

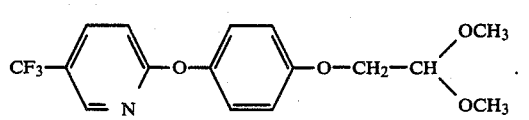

If 2-[4-(5-trifluoromethyl-pyridyl-2-oxy)-phenoxy]-propionic acid and 2-bromoacetaldehyde dimethylacetal are used as starting substances, the course of process (b, variant β) according to the invention can be represented by the following equation:

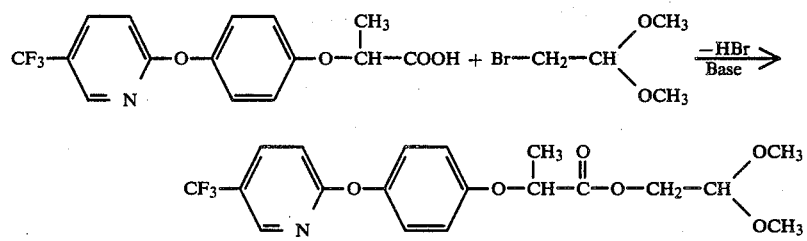

If 4-(5-trifluoromethyl-pyridyl-2-oxy)-phenyl 2,2-dimethoxy-ethyl ether is used as the starting substance and aqueous hydrochloric acid is used as a reactant, the acetal cleavage to be carried out after the reaction by If 2-[4-(5-trifluoromethyl-pyridyl-2-oxy)-phenoxy]-propionyl chloride and 1-hydroxymethyl-1,2,4-triazole are used as starting substances, the course of process (c)

according to the invention can be represented by the following equation:

$$CF_3-\text{pyridyl}-O-\text{phenyl}-O-\overset{CH_3}{\underset{|}{CH}}-CO-Cl + HO-CH_2-N\overset{N=}{\underset{=N}{\diagup}} \xrightarrow[\text{Base}]{-HCl}$$

$$CF_3-\text{pyridyl}-O-\text{phenyl}-O-\overset{CH_3}{\underset{|}{CH}}-COO-CH_2-N\overset{N=}{\underset{=N}{\diagup}}$$

Formula (II) provides a definition of the 4-(pyridyl-2-oxy)-phenols required as starting materials in process (a) according to the invention. In this formula, X and Y have those meanings which have already been mentioned as preferred for X and Y in connection with the substances of the formula (I) according to the invention.

The 4-(pyridyl-2-oxy)-phenols of the formula (II) are already known (compare DE-OS (German Published Specification) No. 2,812,571, DE-OS German Published Specification No. 2,758,002 and U.S. Pat. No. 4,046,553).

The formula (III) provides a definition of the acetals also required as starting substances in process (a, variant α) according to the invention. In this formula, the substituents $R^1$ and $R^3$ preferably have those meanings which have already been mentioned as preferred for these radicals in connection with the description of the substances of the formula (I) according to the invention. Q preferably represents bromine, mesylate or tosylate.

The compounds listed by way of their formulae in Table 11 which follows may be mentioned as examples of acetals of the formula (III):

TABLE 11

$$Q-\overset{R^1}{\underset{|}{CH}}-CH\overset{OR^3}{\underset{OR^3}{\diagup}} \quad (III)$$

| Q | $R^1$ | $R^3$ | $R^3$ |
|---|---|---|---|
| Br | H | CH$_3$ | CH$_3$ |
| Br | CH$_3$ | CH$_3$ | CH$_3$ |
| Br | CH$_3$ | C$_2$H$_5$ | C$_2$H$_5$ |
| Br | CH$_3$ | —CH$_2$—CH$_2$— | |
| Br | H | —CH$_2$—CH$_2$— | |
| Tos—O | CH$_3$ | CH$_3$ | CH$_3$ |
| Mes—O | CH$_3$ | CH$_3$ | CH$_3$ |
| Tos—O | CH$_3$ | C$_2$H$_5$ | C$_2$H$_5$ |
| Tos—O | CH$_3$ | —CH$_2$—CH$_2$— | |
| Mes—O | CH$_3$ | —CH$_2$—CH$_2$— | |

Mes = mesyl
Tos = tosyl

The acetals of the formula (III) are known, or they can be prepared in a simple manner by processes which are known in principle.

To prepare optically active compounds of the formula (I) in which $R^1$ represents methyl, the R- or S-enantiomers of the acetals of the formula (III) in question are required for carrying out process (a, variant α) according to the invention. In this process, the S-enantiomers of the acetals of the formula (III) are used for the synthesis of the R-enantiomers of the compounds of the formula (I), and the R-enantiomers of the acetals of the formula (III) are used for the synthesis of the S-enantiomers of the compounds of the formula (I). The starting substance of the formula (III) therefore has the opposite configuration of the asymmetric carbon atom to the end product, since Walden inversion takes place on the asymmetric carbon atom in the course of the reaction.

The optically active acetals of the formula (III) in which $R^1$ represents methyl are known, or they can be prepared in a simple manner by known processes.

Possible mineral acids which can be used as reactants in carrying out process (a, variant α), in the reaction of the pyridyl-phenyl ethers of the formula (Ia) which is to be effected, if desired, are all the strong mineral acids. Aqueous hydrochloric acid and aqueous sulphuric acid can preferably be used.

Preferred possible carboxylic anhydrides which can be used as reactants in carrying out process (a, variant α), in the reaction of the pyridyl-phenyl ethers of the formula (Ia) which is to be effected, if desired, are anhydrides of aliphatic carboxylic acids. Acetic anhydride and propionic anhydride can preferably be used.

The formula (IV) provides a definition of the alkanecarboxylic acid derivatives required as starting substances in process (a, variant β) according to the invention. In this formula, $R^1$, $R^4$, $R^5$, $R^6$, $R^7$, Z, m and n preferably have those meanings which have already been mentioned as preferred for these radicals and indices in connection with the description of the substances of the formula (I) according to the invention.

The alkanecarboxylic acid derivatives of the formula (IV) are not yet known. They can be prepared by
(d) reacting compounds of the formula $$R^1-CH_2-\overset{O}{\underset{||}{C}}-Z^2 \quad (IX)$$

in which
$R^1$ has the abovementioned meaning and
$Z^2$ represents hydroxyl or chlorine,
with compounds of the formula $$Cl-(\overset{R^4}{\underset{R^5}{C}})_m-(\overset{R^6}{\underset{R^7}{C}})_n-Si(CH_3)_3 \quad (VIa)$$

or $$Q-(\overset{R^4}{\underset{R^5}{C}})_m-(\overset{R^6}{\underset{R^7}{C}})_n-CH\overset{OR^8}{\underset{OR^8}{\diagup}} \quad (VIb)$$

or

-continued

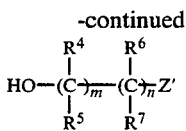

in which

R⁴, R⁵, R⁶, R⁷, R⁸, Q, Z', m and n have the abovementioned meaning,
if appropriate in the presence of an acid-binding agent and if appropriate in the presence of a diluent, and converting the substances thereby formed, of the formula

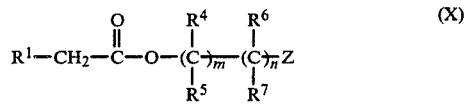

in which $R^1$, $R^4$, $R^5$, $R^6$, $R^7$, Z, m and n have the abovementioned meaning,
into the alkanecarboxylic acid derivatives of the formula (IV) by customary methods, or (e) reacting compounds of the formula

in which $R^1$ and $Z^2$ have the abovementioned meaning and $Z^3$ represents mesylate or tosylate,
with compounds of the formula

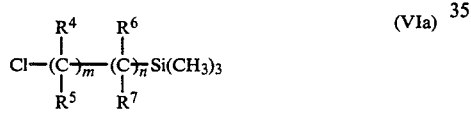

or

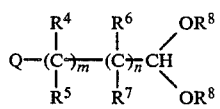

or

in which

R⁴, R⁵, R⁶, R⁷, R⁸, Q, Z', m and n have the abovementioned meaning,
if appropriate in the presence of an acid-binding agent and if appropriate in the presence of a diluent.

The reaction conditions in the abovementioned processes (d) and (e) correspond to those of process (a) according to the invention (compare below).

For the preparation of optically active compounds of the formula (I) in which $R^1$ represents methyl, the R- and S-enantiomers of the alkanecarboxylic acid derivatives of the formula (IV) in question are required in carrying out process (a, variant β) according to the invention. In this process, the S-enantiomers of the alkanecarboxylic acid derivatives of the formula (IV) are used for the synthesis of the R-enantiomers of the formula (I) and the R-enantiomers of the alkanecarboxylic acid derivatives of the formula (IV) are used for the synthesis of the S-enantiomers of the compounds of the formula (I). The starting substance of the formula (IV) in each case has the opposite configuration on the centre of asymmetry to the end product, since Walden inversion takes place on the centre of asymmetry in the course of the reaction.

The optically active alkanecarboxylic acid derivatives of the formula (IV) can be prepared by the above-mentioned process (e) by using the particular optically active compounds of the formula (XI).

Formula (V) provides a definition of the phenoxyalkanecarboxylic acid derivatives required as starting substances in process (b) according to the invention. In this formula, $R^1$ represents hydrogen or methyl. X represents trifluoromethyl or chlorine and Y represents hydrogen or chlorine.

The compounds of the formula (V) are known (compare DE-OS (German Published Specification) No. 2,812,571 and U.S. Pat. No. 4,046,553).

Formula (VIa) provides a definition of the silyl chlorides also required as starting substances in process (b) according to the invention. In this formula, $R^4$, $R^5$, $R^6$, $R^7$, m and n preferably have those meanings which have already been mentioned as preferred for these radicals and indices in connection with the description of the substances of the formula (I) according to the invention.

The substances listed by way of their formulae in Table 12 which follows may be mentioned as examples of compounds of the formula (VIa):

TABLE 12

| | | | | | (VIa) |
|---|---|---|---|---|---|
| $R^4$ | $R^5$ | $R^6$ | $R^7$ | m | n |
| H | H | — | — | 1 | 0 |
| H | H | H | H | 1 | 1 |
| H | H | CH₃ | CH₃ | 1 | 1 |
| H | H | H | H | 2 | 1 |

$$Cl-(C)_m-(C)_n-Si(CH_3)_3$$
with $R^4$, $R^6$ on top and $R^5$, $R^7$ below

The silyl chlorides of the formula (VIa) are known, or they can be prepared in a simple manner by known processes.

Formula (VIb) provides a definition of the acetals which can also be used as starting substances in process (b) according to the invention. In this formula, $R^4$, $R^5$, $R^6$, $R^7$, $R^8$, m and n preferably have those meanings which have already been mentioned as preferred for these radicals and indices in connection with the description of the substances of the formula (I) according to the invention. Q preferably represents bromine, mesylate or tosylate.

The substances listed by way of their formulae in Table 13 which follows may be mentioned as examples of compounds of the formula (VIb):

TABLE 13

| | | | | | | | | (VIb) |
|---|---|---|---|---|---|---|---|---|
| $R^4$ | $R^5$ | $R^6$ | $R^7$ | m | n | $R^8$ | $R^8$ | Q |
| H | H | — | — | 1 | 0 | CH₃ | CH₃ | Br |
| H | H | H | H | 1 | 1 | CH₃ | CH₃ | Br |

TABLE 13-continued $$Q-(C)_m-(C)_n-CH \begin{matrix} R^4 & R^6 & OR^8 \\ | & | & / \\ R^5 & R^7 & \backslash OR^8 \end{matrix} \quad (VIb)$$

| R⁴ | R⁵ | R⁶ | R⁷ | m | n | R⁸ | R⁸ | Q |
|---|---|---|---|---|---|---|---|---|
| H | H | — | — | 1 | 0 | C₂H₅ | C₂H₅ | Br |
| H | H | H | H | 1 | 1 | C₂H₅ | C₂H₅ | Br |
| H | H | — | — | 1 | 0 | —CH₂—CH₂— | | Br |
| H | H | H | H | 1 | 1 | —CH₂—CH₂— | | Br |
| H | H | — | — | 1 | 0 | —(CH₂)₃— | | Br |
| H | H | H | H | 1 | 1 | —(CH₂)₃— | | Br |
| CH₃ | H | — | — | 1 | 0 | CH₃ | CH₂ | OTos |
| CH₃ | H | — | — | 1 | 0 | C₂H₅ | C₂H₅ | OTos |
| CH₃ | H | — | — | 1 | 0 | —CH₂—CH₂— | | OMes |

OMes = mesylate
OTos = tosylate

The compounds of the formula (VIb) are known, or they can be prepared in a simple manner by known methods.

For the preparation of R- and S-enantiomers of the substituted pyridyl-phenyl ethers of the formula (I) in which $R^1$ represents methyl, optically active R- or S-phenoxypropionic acid derivatives of the formula (V) are required as starting substances in carrying out process (b) according to the invention. These optically active phenoxy-propionic acid derivatives are also known (compare DE-OS (German Published Specification) No. 2,758,002).

The R- and S-enantiomers of the phenoxy-propionic acid derivatives of the formula $$X-\underset{N}{\underset{\|}{\bigcirc}}-O-\bigcirc-O-\underset{*}{\overset{CH_3}{\underset{|}{CH}}}-COOH \quad (Va)$$

in which

X and Y have the abovementioned meaning, are obtained by reacting 4-(pyridyl-2-oxy)-phenols of the formula $$X-\underset{N}{\underset{\|}{\bigcirc}}-O-\bigcirc-OH \quad (II)$$

in which

X and Y have the abovementioned meaning, with the S-enantiomers or R-enantiomers of propionic acid derivatives of the formula $$Q-\underset{*}{\overset{CH_3}{\underset{|}{CH}}}-COOR \quad (XII)$$

in which

Q has the abovementioned meaning and
R represents methyl or ethyl, if appropriate in the presence of an acid acceptor, such as, for example, potassium carbonate, and if appropriate in the presence of a diluent, such as, for example, acetonitrile, at temperatures between 0° C. and 120° C., and hydrolysing the esters thereby formed, of the formula $$X-\underset{N}{\underset{\|}{\bigcirc}}-O-\bigcirc-O-\underset{*}{\overset{CH_3}{\underset{|}{CH}}}-COOR \quad (XIII)$$

in which

R, X and Y have the abovementioned meaning, with strong bases, such as, for example, sodium hydroxide, in the presence of a diluent, such as, for example, methanol, ethanol, benzene, toluene or xylene, where appropriate mixed with water, at temperatures between 20° C. and 140° C., and then acidifying the mixture with an acid, such as, for example, hydrochloric acid.

In the first stage of this reaction, Walden inversion takes place at the asymmetric carbon atom of the propionic acid unit.

This means that the R-enantiomers of the phenoxy-propionic acid derivatives of the formula (Va) are formed by reaction of 4-(pyridyl-2-oxy)-phenols of the formula (II) with the S-enantiomers of the propionic acid derivatives of the formula (XII). On the other hand, the S-enantiomers of the phenoxypropionic acid derivatives of the formula (Va) are formed by reaction of 4-(pyridyl-2-oxy)-phenols of the formula (II) with the R-enantiomers of the propionic acid derivatives of the formula (XII).

Formula (VII) provides a definition of the phenoxyalkanecarboxylic acid chlorides required as starting substances in process (c) according to the invention. In this formula, $R^1$ represents hydrogen or methyl. X represents trifluoromethyl or chlorine and Y represents hydrogen or chlorine.

The phenoxyalkanecarboxylic acid chlorides of the formula (VII) are known, or they can be prepared in a simple manner by known processes (compare DE-OS (German Published Specification) No. 2,812,571 and U.S. Pat. No. 4,046,553).

Formula (VIII) provides a definition of the compounds also required as starting substances in process (c) according to the invention. In this formula, $R^4$, $R^5$, $R^6$, $R^7$, m and n preferably have those meanings which have already been mentioned as preferred for these radicals and indices in connection with the description of the substances of the formula (I) according to the invention. Z' represents an optionally substituted azolyl radical which is bonded via a ring nitrogen atom, or a radical of the formula $$-O-\overset{X^1}{\underset{\underset{OR^9}{|}}{P}}\overset{OR^9}{\diagup} \quad \text{or} \quad -CO-N\overset{R^{10}}{\diagup}_{R^{11}}$$

In this context, by azolyl radicals there are preferably to be understood those azolyl radicals which have already been mentioned as preferred in connection with the description of the substances of the formula (I) according to the invention. The substituents $R^9$, $R^{10}$, $R^{11}$ and $X^1$ preferably have those meanings which have already been mentioned as preferred for these radicals in connection with the description of the substances of the formula (I) according to the invention.

Specific examples of azolyl compounds of the formula (VIII) which may be mentioned are: 1-hydroxymethylpyrazole, 1-(1-hydroxyethyl)-pyrazole, 1-hydroxymethylimidazole, 1-(1-hydroxyethyl)-imidazole, 1-hydroxymethyl-1,2,4-triazole, 1-(1-hydroxyethyl)-1,2,4-triazole, 1-hydroxymethyl-1,3,4-triazole, 1-(1-hydroxyethyl)-1,3,4-triazole, 1-hydroxymethyl-3,5-dimethyl-pyrazole, 1-hydroxymethyl-2-methyl-imidazole, 1-hydroxymethyl-3-methyl-pyrazole, 3-chloro-1-hydroxymethyl-1,2,4-triazole, 4-chloro-1-hydroxymethyl-pyrazole, 1-hydroxymethyl-4-methyl-pyrazole, 1-hydroxymethyl-4-methoxypyrazole, 4-chloro-1-hydroxymethyl-3,5-dimethyl-pyrazole, 1-(2-hydroxyethyl)-pyrazole, 1-(2-hydroxyethyl)-imidazole and 1-(hydroxy-1,1-dimethyl-ethyl)-1,2,4-triazole.

The azolyl compounds of the formula (VIII) are already known (compare DE-OS (German Published Specification No. 2,835,157 and DE-OS (German Published Specification) No. 2,835,158).

The substances listed in Tables 14 and 15 which follow may be mentioned as examples of those compounds of the formula (VIII) in which Z' represents the radicals of the formulae

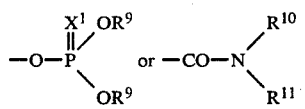

TABLE 14

(VIIIa)

$$HO-(C)_m-(C)_n-O-P\begin{matrix}X^1 & OR^9\\ \| \diagup \\ \diagdown \\ OR^9\end{matrix}$$

with substituents $R^4, R^5$ on first C and $R^6, R^7$ on second C.

| $R^4$ | $R^5$ | $R^6$ | $R^7$ | m | n | $X^1$ | $R^9$ | $R^9$ |
|---|---|---|---|---|---|---|---|---|
| H | H | H | H | 1 | 1 | O | $CH_3$ | $CH_3$ |
| H | H | H | H | 1 | 1 | S | $CH_3$ | $CH_3$ |
| H | H | H | H | 1 | 1 | O | $C_2H_5$ | $C_2H_5$ |
| H | H | H | H | 1 | 1 | S | $C_2H_5$ | $C_2H_5$ |
| H | H | H | H | 1 | 1 | O | $C_3H_7-n$ | $C_3H_7-n$ |
| H | H | H | H | 1 | 1 | S | $C_3H_7-n$ | $C_3H_7-n$ |

TABLE 15

(VIIIb)

$$HO-(C)_m-(C)_n-CO-N\begin{matrix}R^{10}\\ \diagup \\ \diagdown \\ R^{11}\end{matrix}$$

| $R^4$ | $R^5$ | $R^6$ | $R^7$ | n | n | $R^{10}$ | $R^{11}$ |
|---|---|---|---|---|---|---|---|
| H | H | — | — | 1 | 0 | $CH_3$ | $CH_3$ |
| H | H | H | H | 1 | 1 | $CH_3$ | $CH_3$ |
| H | H | — | — | 1 | 0 | $C_2H_5$ | $C_2H_5$ |
| H | H | H | H | 1 | 1 | $C_2H_5$ | $C_2H_5$ |
| H | H | — | — | 1 | 0 | $C_3H_7-n$ | $C_3H_7-n$ |
| H | H | H | H | 1 | 1 | $C_3H_7-n$ | $C_3H_7-n$ |

The compounds of the formulae (VIIIa) and (VIIIb) are known, or they can be prepared in a simple manner by known methods.

To prepare the R- and S-enantiomers of the substituted pyridyl-phenyl ethers of the formula (I) in which $R^1$ represents methyl, optically active R- or S-phenoxypropionyl chlorides of the formula

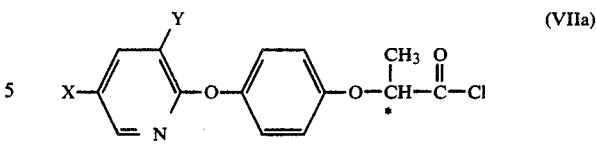

in which

X and Y have the abovementioned meaning, are required as starting substances in carrying out process (c) according to the invention. These starting substances can be prepared from the particular acid on which they are based by customary methods, for example by chlorination with thionyl chloride (compare DE-OS (German Published Specification) No. 2,758,002).

Processes (a), (b) and (c) according to the invention for the preparation of the new substituted pyridyl-phenyl ethers of the formula (I) are preferably carried out using diluents. Possible diluents are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and dimethylsulphoxide, tetramethylenesulphone and hexamethylphosphoric acid triamide.

Diluents which can be used for the reaction of substituted pyridyl-phenyl ethers of the formula (Ia) optionally to be carried out in process (a, variant α) according to the invention are all the diluents customary for such acetal cleavage reactions. Water is preferably used.

Acid-binding agents which can be used both in processes (a) and (b) according to the invention and in process (c) are all the acid-binding agents which can customarily be used for such reactions. Preferred possible agents are alkali metal hydroxides, such as, for example, sodium hydroxide and potassium hydroxide, alkali metal carbonates and alcoholates, such as sodium carbonate and potassium carbonate and sodium methylate and ethylate and potassium methylate and ethylate, and furthermore aliphatic, aromatic or heterocyclic amines, for example triethylamine, trimethylamine, dimethylaniline, dimethylbenzylamine, pyridine, 1,5-diaza-bicyclo-[4.3.0]-non-5-ene and 1,8-diaza-bicyclo[5.4.0]-undec-7-ene (DBU).

The reaction temperatures can be varied within a substantial range both in process (a) according to the invention and in processes (b) and (c). Processes (a), (b) and (c) are in general each carried out at temperatures between −20° C. and +160° C., preferably between 0° C. and 140° C. The reaction of compounds of the formula (Ia) which is to be carried out, if desired, in process (a, variant α) is in general effected at temperatures between 50° C. and 140° C., preferably between 80° C. and 120° C.

Processes (a), (b) and (c) according to the invention are in general carried out under normal pressure. However, it is also possible to carry them out under increased or reduced pressure.

For carrying out processes (a), (b) and (c) according to the invention, the particular starting substances required are in general used in approximately equimolar amounts. However, it is also possible to use one of the two particular components employed in a larger excess. The reactions are in general carried out in a suitable diluent in the presence of an acid acceptor, and the reaction mixture is stirred at the particular temperature required for several hours. Working up in processes (a), (b) and (c) according to the invention is in each case effected by customary methods.

In carrying out the acetal cleavage to be effected if desired, in process (a, variant α), a catalytic amount or an excess of dilute mineral acid or carboxylic anhydride is employed per mol of substituted pyridyl-phenyl ether of the formula (Ia). The reaction is in general carried out in the presence of a diluent, and the reaction mixture is stirred at the required temperature for several hours. The reaction is carried out and the mixture is worked up by customary methods (compare Houben-Weyl VII, 1, page 427 et seq.).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellariva, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used for selectively combating weeds in dicotyledon crops and in cereals and rice.

The active compounds can be converted to the customary formulations, such as solutions, emulsions, wettable powders, suspensions, powders, dusting agents, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzene, chloroethylene or methylene chloride, aliphatic hydrocarbons, such as cyclohexane or paraffins, for example mineral oil fractions and mineral and vegetable oils, alcohols, such as butanol or glycol as well as their esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates and furthermore ammonium salts; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulation or tank mixing being possible.

The mixtures can contain known herbicides, such as, for example, 1-amino-6-ethylthio-3-(2,2-dimethylpropyl)-1,3,5-triazine-2,4(1H,3H)-dione or N-(2-benzthiazolyl)-N,N'-dimethylurea for combating weeds in cereals; 4-amino-3-methyl-6-phenyl-1,2,4-triazin-5(4H)-one for combating weeds in sugar-beet, and 4-amino-6-(1,1-dimethylethyl)-3-methylthio-1,2,4-triazin-5(4H)-one for combating weeds in soya beans. Surprisingly, some mixtures also show a synergistic action.

Mixtures with other known active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders and granules. They are used in the customary manner, for example by watering, spraying, atomising or scattering.

The active compounds according to the invention can be applied before or after emergence of the plants.

They can also be incorporated into the soil before sowing.

The amount of active compound used can vary within a substantial range. It depends essentially on the nature of the desired effect. In general, the amounts used are between 0.05 and 10 kg of active compound per ha, preferably between 0.1 and 5 kg/ha.

The present invention also provides a herbicidal composition containing as active ingredient a compound of the formula (I) according to the present invention in admixture with a solid diluent or carrier or in admixture with a liquid diluent or carrier containing a surface-active agent.

The present invention also provides a method of combating weeds which comprises applying to the weeds, or to a habitat thereof, a compound of the formula (I) according to the present invention alone or in the form of a composition containing as active ingredient a compound of the formula (I) according to the present invention in admixture with a diluent or carrier.

PREPARATION EXAMPLES

Example 1

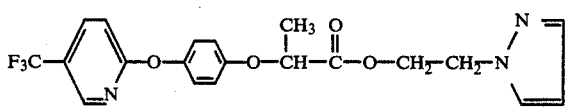

A solution of 8.6 g (0.025 mol) of 2-[4-(5-trifluoromethylpyridyl-2-oxy)-phenoxy]-propionyl chloride in 35 ml of toluene was added to a solution of 2.8 g (0.025 mol) of 1-(2-hydroxyethyl)-pyrazole and 2.8 g (0.0275 mol) of triethylamine in 50 ml of toluene at 0° to 5° C., while stirring. The mixture was stirred at room temperature for a further 16 hours and was then worked up by first adding toluene and then washing successively with dilute hydrochloric acid and water, drying and concentrating under reduced pressure. The residue which remained was freed from traces of volatile constituents by slightly warming under a high vacuum. 7.5 g (71.3% of theory) of 2-(pyrazol-1-yl)-ethyl 2-[4-(5-trifluoromethylpyridyl-2-oxy)-phenoxy]-propionate were obtained in this manner in the form of a yellow oil of refractive index $n_D^{21.5} = 1.5258$.

Example 2

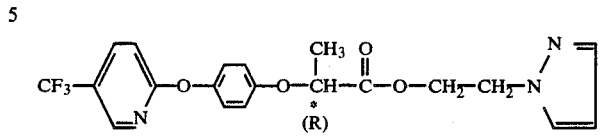

A solution of 6 g (0.0175 mol) of the R-enantiomer of 2-[4-(5-trifluoro-methyl-pyridyl-2-oxy)-phenoxy]-propionyl chloride in 50 ml of toluene was added to a solution of 2 g (0.0175 mol) of 1-(2-hydroxyethyl)-pyrazole and 1.9 g (0.019 mol) of triethylamine in 50 ml of toluene at 0° to 5° C., while stirring. The reaction mixture was stirred at room temperature for a further 16 hours and was then worked up by adding water, washing the organic phase successively with dilute aqueous hydrochloric acid and water and then drying it and concentrating it under reduced pressure. The residue which remained was freed from traces of volatile constituents by warming slightly under a high vacuum. 5.2 g (70.6% of theory) of the R-enantiomer of 2-(pyrazol-1-yl)-ethyl 2-[4-(5-trifluoromethyl-pyridyl-2-oxy)-phenoxy]-propionate were obtained in this manner in the form of an oil of refractive index $n_D^{21} = 1.5286$.

Optical rotation: $[\alpha]_D^{24} = +12.7°$: (1-molar solution in chloroform; cell length 10 cm).

The compounds of the formula (V) shown by way of their formulae in the following examples are obtained in an analogous manner.

Example 3

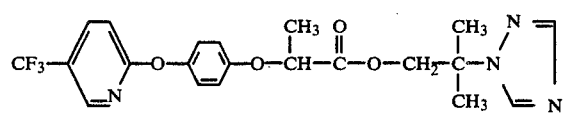

Yield: 52.4% of theory. $n_D^{21.5} = 1.5193$.

Example 4

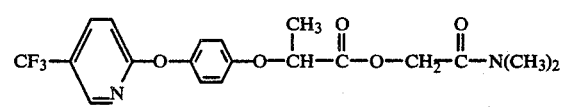

Yield: 50.5% of theory. $n_D^{21.5} = 1.5210$.

Example 5

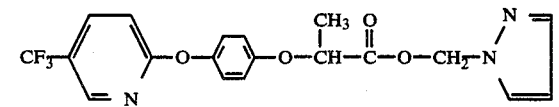

Yield: 75.7% of theory. $n_D^{21.5} = 1.5265$.

Example 6

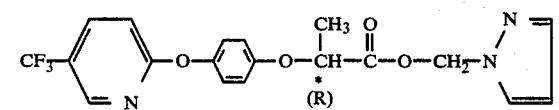

Yield: 74.4% of theory.
Refractive index with $n_D^{20.5} = 1.5270$.
Optical rotation: $[\alpha]_D^{24} = 12.4°$: (1-molar solution in chloroform; cell length 10 cm).

Example 7

[Structure: CF$_3$-pyridyl-O-phenyl-O-CH(CH$_3$)-C(O)-O-CH$_2$-CH$_2$-O-P(=S)(OC$_2$H$_5$)$_2$]

Yield: 51.5% of theory. $n_D^{21.5} = 1.5058$.

Example 8

[Structure: CF$_3$-pyridyl-O-phenyl-O-CH*(CH$_3$)(R)-C(O)-O-CH$_2$-CH$_2$-O-P(=S)(OC$_2$H$_5$)$_2$]

Yield: 81.9% of theory.
Refractive index: $n_D^{21} = 1.5077$.
Optical rotation: $[\alpha]_D^{24} = +11.2°$: (1-molar solution in chloroform; cell length 10 cm).

Example 9

[Structure: 3,5-dichloro-pyridyl-O-phenyl-O-CH(CH$_3$)-C(O)-O-CH$_2$-N(pyrazolyl)]

Yield: 94.1% of theory.
Melting point: 87° C.

Example 10

[Structure: 3,5-dichloro-pyridyl-O-phenyl-O-CH*(CH$_3$)(R)-C(O)-O-CH$_2$-N(pyrazolyl)]

Yield: 65.8% of theory.
Refractive index: $n_D^{20.5} = 1.5804$.
Optical rotation: $[\alpha]_D^{24} = +8.8°$: (1-molar solution in chloroform; cell length 10 cm).

Example 11

[Structure: 3,5-dichloro-pyridyl-O-phenyl-O-CH(CH$_3$)-C(O)-O-C$_2$H$_4$-N(pyrazolyl)]

Yield: 65.9% of theory.
Melting point: 58° C.

Example 12

[Structure: 3,5-dichloro-pyridyl-O-phenyl-O-CH*(CH$_3$)(R)-C(O)-O-C$_2$H$_4$-N(pyrazolyl)]

Yield: 77.2% of theory.
Refractive inex: $n_D^{20.5} = 1.5755$.
Optical rotation $[\alpha]_D^{24} = +10.8°$.

Example 13

[Structure: 3,5-dichloro-pyridyl-O-phenyl-O-CH(CH$_3$)-C(O)-O-CH$_2$-CH$_2$-O-P(=S)(OC$_2$H$_5$)$_2$]

Yield: 75.6% of theory.
$n_D^{19.5}$: 1.5461.

Example 14

[Structure: 3,5-dichloro-pyridyl-O-phenyl-O-CH*(CH$_3$)(R)-C(O)-O-CH$_2$-CH$_2$-O-P(=S)(OC$_2$H$_5$)$_2$]

Yield: 69.8% of theory.
Refractive index: $n_D^{20.5} = 1.5465$.
Optical rotation: $[\alpha]_D^{24} = +9.7°$: (1-molar solution in chloroform; cell length 10 cm.

Example 15

[Structure: CF$_3$-pyridyl-O-phenyl-O-CH(CH$_3$)-C(O)-O-CH$_2$-Si(CH$_3$)$_3$]

8.4 g (0.055 mol) of 1,5-diaza-bicyclo-[5,4.0]undecene ("DBU") were added to a solution of 16.5 g (0.05 mol) of 2-[4-(5-trifluoromethyl-pyridyl-2-oxy)-phenoxy]-propionate in 100 ml of acetone at 20° C., while stirring. The reaction mixture, in which a precipitate formed was stirred at room temperature for a further 30 minutes, and 6.1 g (0.05 mol) of chloromethyl-trimethylsilane were then added at 20° C. The reaction mixture was boiled under reflux for 6.5 hours and was then cooled, and concentrated by stripping off the solvent. The residue which remained was dissolved in methylene chloride and the resulting organic phase was washed successively with aqueous sodium hydroxide solution, dilute aqueous hydrochloric acid and water and, after drying, was concentrated. The residue was taken up once more in methylene chloride and was purified again in the manner described above. 6.4 g (31% of theory) of (trimethylsilyl)-methyl 2-[3-(5-trifluoromethyl-pyridin-2-oxy)phenoxy]-propionate were thereby obtained.

$n_D^{21.5} = 1.4984$.

The compounds shown by way of their formulae in the examples which follow were also obtained by the method described in Example 15.

Example 16

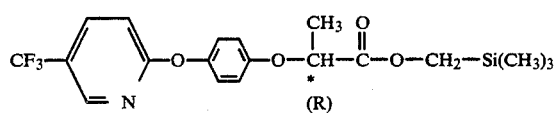

Yield: 63% of theory.
Refractive index: $n_D^{20.5} = 1.4975$.
Optical rotation: $[\alpha]_D^{24} = +14.9°$: (1-molar solution in chloroform; cell length 10 cm).

Example 17

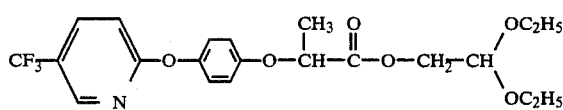

Yield: 58.7% of theory.
$n_D^{21.5} = 1.4935$.

Example 18

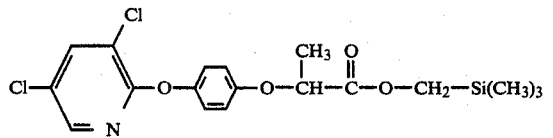

Yield: 87% of theory.
$n_D^{21.5} = 1.5474$.

Example 19

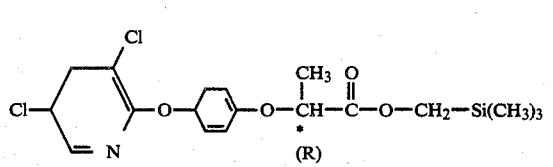

Yield: 24.2% of theory.
Refractive index: $n_D^{23.5} = 1.5433$.
Optical rotation: $[\alpha]_D^{24} = +15.4°$.

Example 20

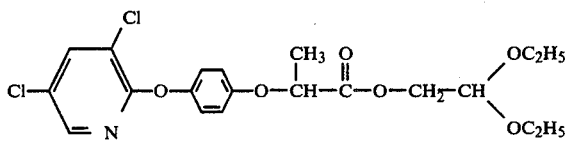

Yield: 45% of theory.
$n_D^{19.5} = 1.5353$: (1-molar solution in chloroform; cell length 10 cm).

Example 21

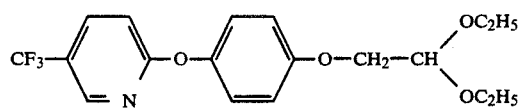

4.9 g (0.025 mol) of bromoacetaldehyde diethylacetal were added to a mixture of 6.4 g (0.025 mol) of 4-(5-trifluoromethyl-pyridyl-2-oxy)-phenol, 2.6 g (0.019 mol) of potassium carbonate and 50 ml of dimethylsulphoxide at 120° C., while stirring. The reaction mixture was stirred at 120° C. for a further 6 hours and was then cooled and poured into water. It was extracted several times with methylene chloride, the organic phase was washed successively with dilute aqueous sodium hydroxide solution and water and was then dried and the solvent was stripped off. The residue which remained was freed from traces of volatile constituents by slightly warming under a high vacuum. 4 g (43.1% of theory) of 4-(5-trifluoromethyl)-pyridyl-2-oxy)-phenyl 2,2-diethoxyethyl ether were obtained in this manner in the form of an oil.

$n_D^{20} = 1.4965$.

The compound shown by way of its formula in Example 22 which follows was also obtained by the method described in Example 21.

Example 22

Cl-pyridine-O-phenyl-O-CH₂-CH(OC₂H₅)₂ structure

Yield: 67.2% of theory.
Melting point: 67° C.

Preparation of starting substances

Example 23

$$CH_3\text{-}C_6H_4\text{-}SO_2\text{-}O\text{-}\underset{*}{CH}(CH_3)\text{-}C(=O)\text{-}O\text{-}CH_2\text{-}CH_2\text{-}N\text{(pyrazole)}$$ (IV-1)

(S)

5.25 g (0.02 mol) of the S-enantiomer of lactyl chloride tosylate were added to a mixture of 2.24 g (0.02 mol) of 1-(2-hydroxyethyl)-pyrazole, 2 g (0.02 mol) of triethylamine and 50 ml of toluene at 20° C., while stirring. The reaction mixture was stirred at 20° C. for a further 14 hours and then worked up by adding water, extracting the mixture several times with toluene, drying the combined organic phases and concentrating them by stripping off the solvent under reduced pressure. 4.7 g (69.5% of theory) of the S-enantiomer of 2-(pyrazol-1-yl)-ethyl 2-tosyloxy-propionate were obtained in this manner.

Optical rotation: $[\alpha]_D^{24} = -11.4°$: (1-molar solution in chloroform; cell length 10 cm).

Example 24

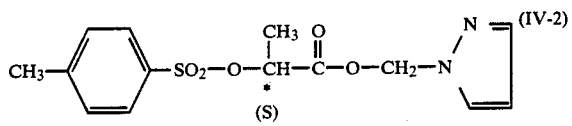

The compound of the formula shown above was also prepared by the method described in Example 23.
Yield: 60% of theory
Optical rotation: $[\alpha]_D^{24} = -13.7°$ C.: (1-molar solution in chloroform; cell length 10 cm).

Example 25

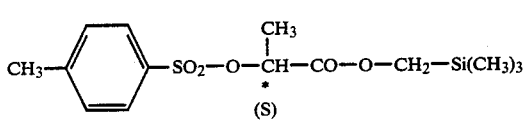

The compound of the formula shown above was also prepared by the method described in Example 23.
Yield: 76% of theory
Optical rotation: $[\alpha]_D^{24} = -11.4°$: (1-molar solution in chloroform; cell length 10 cm).

The following compounds were used as comparison substances in the biological tests described below:

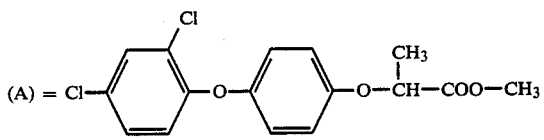

Methyl 2-[4-(2,4-dichlorophenoxy)-phenoxy]-propionate (known from DE-OS (German Published Specification) No. 2,223,894).

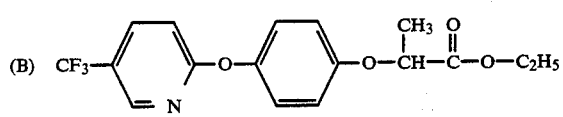

Ethyl 2-[4(5-trifluoromethyl-pyridyl-2-oxy)-phenoxy]-propionate (known from DE-OS (German Published Specification) No. 2,812,571)

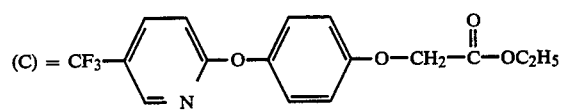

Ethyl [4-(5-trifluoromethyl-pyridyl-2-oxy)-phenoxy]-acetate (known from DE-OS (German Published Specification) No. 2,812,571)

Example A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, active compound (18) according to the invention exhibited a better selective herbicidal activity than the comparison substances (A), (B) and (C).

Example B

Post-emergence test.
Solvent: 5 parts by weight of acetone.
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, the compound according to Example (19) exhibited a very good selective herbicidal activity.

It will be understood that the specification and examples are illustrative, but not limitative of the present invention and that other embodiments within the spirit and scope of the invention will suggest themselves to those skilled in the art.

What is claimed is:

1. A racemate or the K- or S-enantiomer of a substituted pyridyl-phenyl ether compound of the formula

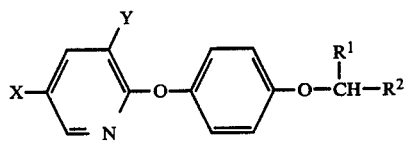

in which

X represents trifluoromethyl or chlorine,
Y represents hydrogen or chlorine
$R^1$ represents hydrogen or methyl and
$R^2$ represents the radicals of the formula

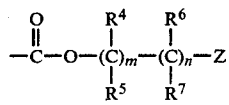

wherein
$R^4$, $R^5$, $R^6$ and $R^7$ independently of one another represent hydrogen or methyl,
m represents 1 to 2
n represents 0 or 1 and
Z represents a radical of the formula $$-O-P\begin{matrix}X^1\\\|\end{matrix}\diagup\begin{matrix}OR^9\\\\OR^9\end{matrix}$$

in which
$R^9$ represents alkyl with 1 to 4 carbon atoms
$X^1$ represents oxygen or sulfur
$R^{10}$ and $R^{11}$ independently of one another represent hydrogen or alkyl with 1 to 4 carbon atoms.

2. A compound according to claim 1 wherein Z represents a radical of the formula $$-O-P\begin{matrix}X^1\\\|\end{matrix}\diagup\begin{matrix}OR^9\\\\OR^9\end{matrix}$$

3. A compound according to claim 1, designated 2-(O,O-diethyl-thiono-phosphoryl)-ethyl 2-[4,(5,trifluoromethylpyridyl-2-oxy)-phenoxy]-propionate of the formula

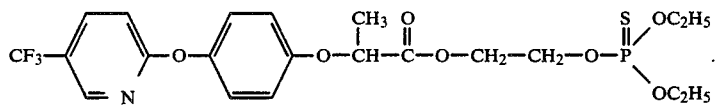

4. A compound according to claim 1, of the formula

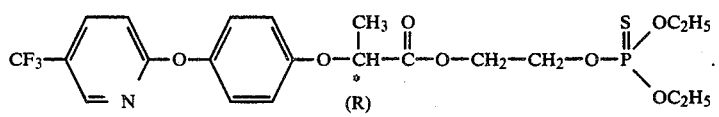

5. A compound according to claim 1, of the formula

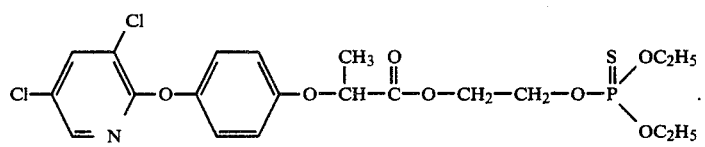

6. A compound according to claim 1, of the formula

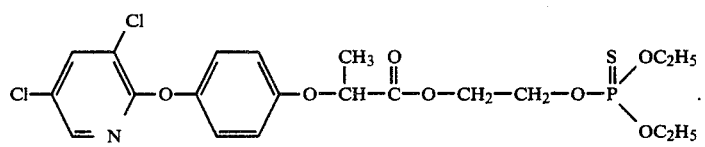

7. A herbicidal composition comprising an agriculturally acceptable carrier and, in a herbicidally effective amount, a substituted pyridyl-phenyl ether as claimed in claim 1.

8. A herbicidal composition as claimed in claim 7, containing from 0.1 to 95% by weight of the active compound.

9. A method of combating weeds, which comprises applying to the weeds, or to their habitat, a herbicidally effective amount of a substituted pyridyl-phenyl ether as claimed in claim 1.

10. A method as claimed in claim 9, wherein said compound is applied at a dosage of 0.05 to 10 kg per hectare.

11. A method as claimed in claim 10, wherein said compound is applied at a dosage of 0.1 to 5 kg per hectare.

12. A method as claimed in claim 9, wherein said substituted pyridyl-phenyl ether is selected from the group consisting of

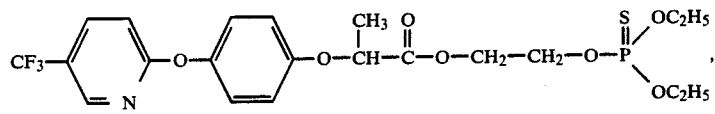
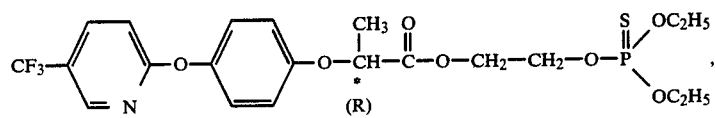
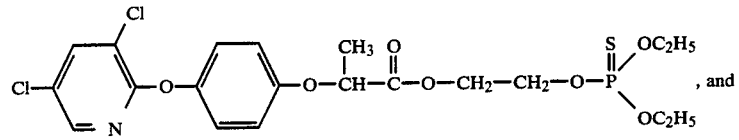
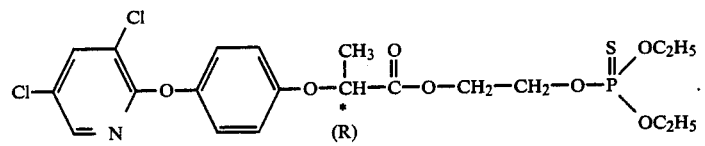

UNITED STATES PATENT AND TRADEMARK OFFICE
CERTIFICATE OF CORRECTION

PATENT NO. : 4,657,577

DATED : April 14, 1987

INVENTOR(S) : Heinz Förster, et al.

It is certified that error appears in the above-identified patent and that said Letters Patent is hereby corrected as shown below:

Col. 25, line 36      Delete "Stellariva" and substitute --Stellaria--

Col. 30, line 25      Correct spelling of --index--

Col. 30, line 45      After "-O-" first instance, insert

Col. 32, line 11      Delete "1.5353" and substitute --1.5352--

Col. 34, line 59      Delete "K-" and substitute --R- --

Signed and Sealed this

Thirty-first Day of May, 1988

Attest:

DONALD J. QUIGG

Attesting Officer      Commissioner of Patents and Trademarks